US010886091B2

(12) United States Patent
Demcko et al.

(10) Patent No.: US 10,886,091 B2
(45) Date of Patent: Jan. 5, 2021

(54) FEEDTHROUGH DEVICE INCLUDING A GAS DISCHARGE TUBE

(71) Applicant: AVX Corporation, Fountain Inn, SC (US)

(72) Inventors: Ronald Stephan Demcko, Raleigh, NC (US); Michael W. Kirk, Simponsivlle, SC (US)

(73) Assignee: AVX Corporation, Fountain Inn, SC (US)

( * ) Notice: Subject to any disclaimer, the term of this patent is extended or adjusted under 35 U.S.C. 154(b) by 0 days.

(21) Appl. No.: 16/505,796

(22) Filed: Jul. 9, 2019

(65) Prior Publication Data

US 2020/0020500 A1 Jan. 16, 2020

Related U.S. Application Data

(60) Provisional application No. 62/696,027, filed on Jul. 10, 2018.

(51) Int. Cl.
*H01J 1/24* (2006.01)
*H01J 17/04* (2012.01)
*A61N 1/375* (2006.01)

(52) U.S. Cl.
CPC .............. *H01J 1/24* (2013.01); *H01J 17/04* (2013.01); *A61N 1/3754* (2013.01); *H01J 2261/385* (2013.01)

(58) Field of Classification Search
CPC .................................................. A61N 1/3754
See application file for complete search history.

(56) References Cited

U.S. PATENT DOCUMENTS

| 6,643,903 B2 | 11/2003 | Stevenson et al. |
| 6,721,155 B2 | 4/2004 | Ryman |
| 7,199,995 B2 | 4/2007 | Stevenson |
| 8,659,870 B2 * | 2/2014 | Brendel ................... H01G 4/35 361/302 |

(Continued)

FOREIGN PATENT DOCUMENTS

CN      106252180 B      10/2017

OTHER PUBLICATIONS

AVX EMI Filters, 61 pages.

(Continued)

*Primary Examiner* — Joseph L Williams
*Assistant Examiner* — Jacob R Stern
(74) *Attorney, Agent, or Firm* — Dority & Manning, P.A.

(57) ABSTRACT

A feedthrough device for protecting a system from an electrical transient may include a housing having a first end and a second end spaced apart from the first end in a longitudinal direction. A conductive line may extend through the housing from the first end to the second end of the housing. The conductive line may define an input end proximate the first end of the housing and an output end proximate the second end of the housing for connecting the feedthrough device with the system to be protected. A filter may be disposed within the housing and coupled with the conductive line at a first location. A gas discharge tube may be disposed within the housing and coupled with the conductive line at a second location on the conductive line that is proximate the filter and between the input end of the conductive line and the first location.

16 Claims, 7 Drawing Sheets

(56) References Cited

U.S. PATENT DOCUMENTS

| | | |
|---|---|---|
| 8,854,153 B2 | 10/2014 | Kauffman |
| 9,279,425 B2 | 3/2016 | Tolbert, Jr. et al. |
| 2016/0186737 A1 | 6/2016 | Tolbert, Jr. et al. |

OTHER PUBLICATIONS

Combining GDTs and MOVs for Surge Protection of AC Power Lines from Littelfuse, Jan. 2002, 4 pages.
Hybrid DC Blocked Coaxial Surge Protector, CXP Series, from Citel, Inc., 1 page.
International Search Report and Written Opinion for PCT/US2019/040992 dated Nov. 8, 2019, 16 pages.

* cited by examiner

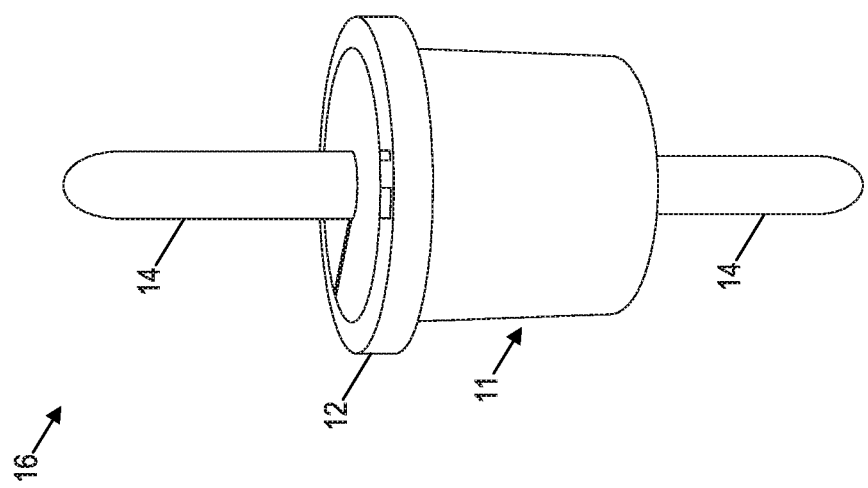
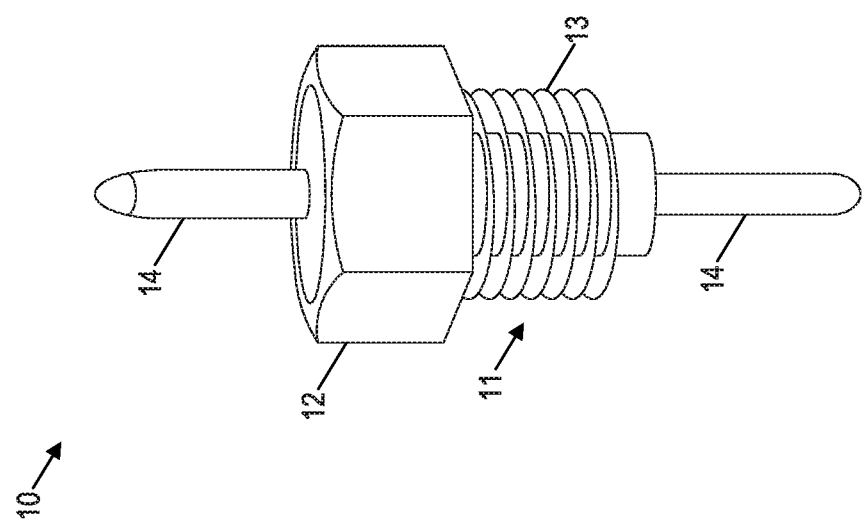

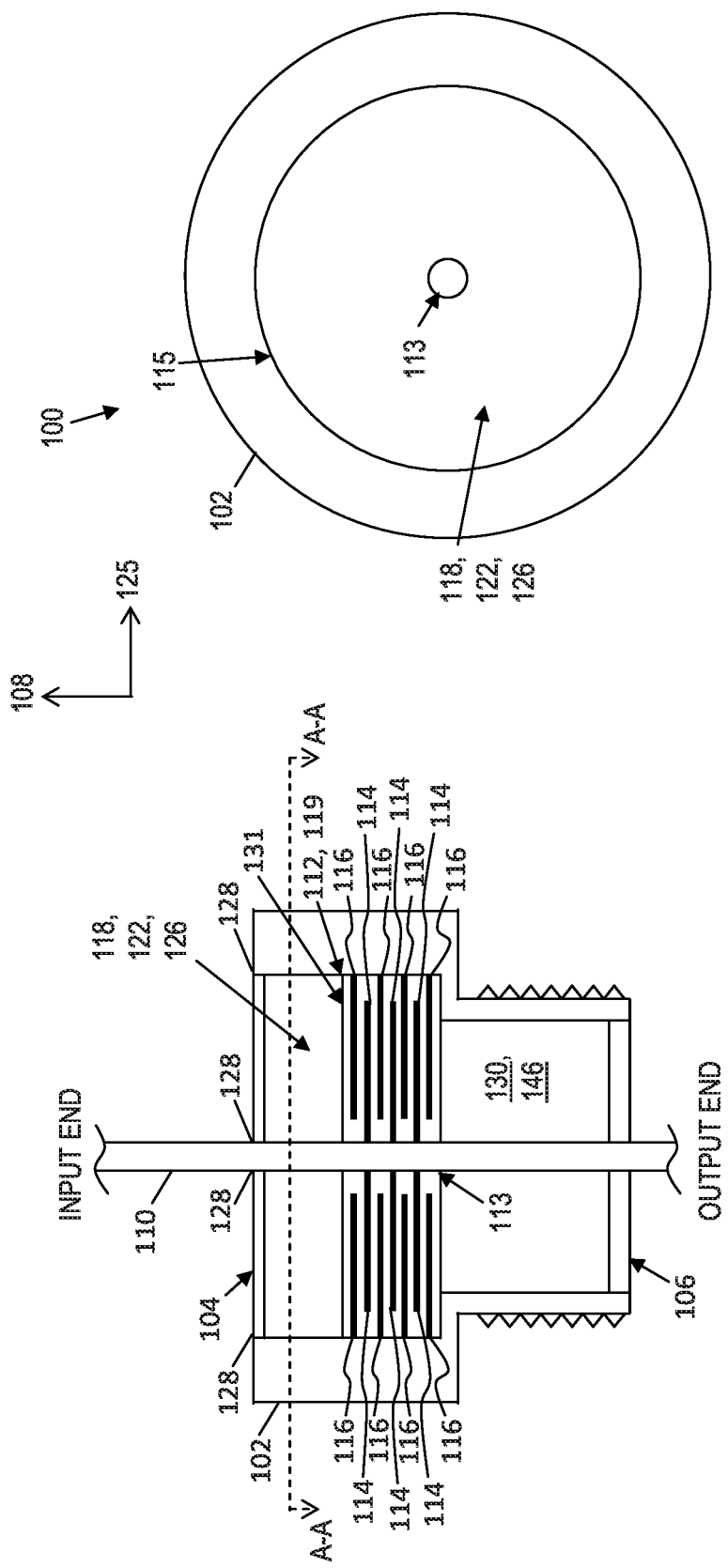

FEEDTHROUGH DEVICE INCLUDING A GAS DISCHARGE TUBE

RELATED APPLICATIONS

This application claims priority to and the benefit of U.S. Provisional Patent Application No. 62/696,027 filed on Jul. 10, 2018, which is incorporated herein by reference in its entirety.

BACKGROUND OF THE INVENTION

Electrical transients such as current surges and voltage spikes can damage electrical devices and systems. In many applications, electrical devices are interconnected via wiring that passes through a structure. For example, vehicles such as planes and helicopters, wiring often passes through structural components, such as ribs or bulkheads, to connect various devices. To protect electrical devices from electrical transients passing through such wiring, feedthrough devices may be used to facilitate interconnection of the various components. Feedthrough devices may be configured to divert electrical transients to ground, such as the structural component to which the device is mounted.

Existing feedthrough devices, however, may not be configured to divert electrical transients in a manner that protects the feedthrough device itself from damage. As a result, the feedthrough device may become inoperable after experiencing a small number of electrical transients, leaving the device or system unprotected. As an example, electromagnetic pulses (EMPs) can be weaponized to damage electronics in vehicles. Feedthrough devices that fail after a few electrical transients can leave the vehicle unprotected and susceptible to subsequent EMPs. Accordingly, an improved feedthrough device that addresses one or more of the issues identified above would be welcomed in the technology.

SUMMARY OF THE INVENTION

In accordance with one embodiment of the present disclosure, a feedthrough device for protecting a system from an electrical transient may include a housing. The housing may have a first end and a second end spaced apart from the first end in a longitudinal direction. A conductive line may extend through the housing from the first end to the second end of the housing. The conductive line may define an input end proximate the first end of the housing and an output end proximate the second end of the housing for connecting the feedthrough device with the system to be protected. A filter may be disposed within the housing and coupled with the conductive line at a first location. A gas discharge tube may be disposed within the housing and coupled with the conductive line at a second location on the conductive line that is proximate the filter and between the input end of the conductive line and the first location.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures, in which:

FIG. 1A illustrates one embodiment of a feedthrough device that can be threaded into a tapped hole in a bulkhead according to aspects of the present disclosure;

FIG. 1B illustrates another feedthrough device that is configured to be soldered, press fit, or otherwise secured in a hole in the bulkhead according to aspects of the present disclosure;

FIG. 4A illustrates a simplified schematic diagram of another embodiment of a feedthrough device according to aspects of the present disclosure;

FIG. 4B illustrates a section view of the feedthrough device of FIG. 4A along section A-A;

Figure 2B:
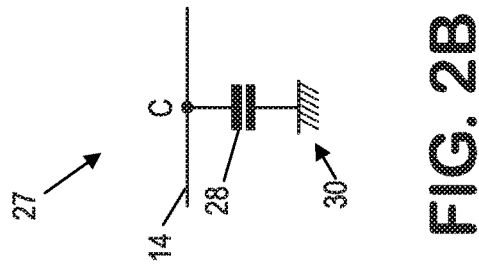
FIG. 2B illustrates an example configuration for the filter of the feedthrough device of FIG. 2A or FIG. 2C.

Repeat use of reference characters in the present specification and drawings is intended to represent same or analogous features or elements of the invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

Generally speaking, the present disclosure is directed to a feedthrough device for protecting a system from an electrical transient. The feedthrough device may include a housing having a first end and a second end spaced apart from the first end in a longitudinal direction. A conductive line may extend through the housing from the first end to the second end of the housing. The conductive line may define an input end proximate the first end of the housing and an output end proximate the second end of the housing for connecting the feedthrough device with the system to be protected. A filter may be disposed within the housing and coupled with the conductive line at a first location. A gas discharge tube may be disposed within the housing and coupled with the conductive line at a second location on the conductive line that is proximate the filter and between the input end of the conductive line and the first location.

The gas discharge tube may include any suitable gas or gas mixture capable of being ionized. For example, the gas discharge tube may include at least one noble gas (e.g., helium, neon, argon, krypton, xenon, or mixtures thereof). In some embodiments, the gas discharge tube may include a metal vapor, such as a vapor of mercury, sodium, sulfur or any other suitable metal, either alone or in combination with a gas, such as a noble gas. The gas or gas mixture may be selected based on various desired properties, design considerations, and/or physical characteristics of the gas discharge tube. For example, the properties may include a desired breakdown voltage, current handling ability, repetitive surge handling capability, etc. Physical characteristics may include a volume of the gas or gas mixture, a physical dimension of the gas discharge tube (e.g., a dimension of a container which the gas or gas mixture is disposed), a material of the gas discharge tube (e.g., a material of a container within which the gas or gas mixture is disposed), etc.

In some embodiments, the filter may include a multilayer ceramic capacitor. The multilayer ceramic capacitor may include a dielectric material. For example, the dielectric material may include a ceramic, semiconductive, or insulating material, such as but not limited to barium titanate, calcium titanate, zinc oxide, alumina with low-fire glass, or other suitable ceramic or glass-bonded materials. Alternatively, the dielectric material may be an organic compound such as an epoxy (with or without ceramic mixed in, with or without fiberglass), popular as circuit board materials, or other plastics common as dielectrics. In these cases, the conductor is usually a copper foil which is chemically etched to provide the patterns. In still further embodiments, dielectric material may comprise a material having a relatively high dielectric constant (K), such as one of NPO (COG), X7R, X5R X7S, Z5U, Y5V and strontium titanate. The dielectric constant of the dielectric material may range from about 100 to about 25,000, in some embodiments from about 200 about 10,000, and in some embodiments, from about 500 to about 9,000, such as determined in accordance with ASTM D2149-13 at operating temperatures ranging from about −55° C. to about 150° C. (e.g., 25° C.) and frequencies ranging from about 100 Hz to about 1 GHz (e.g., 1 kHz).

The multilayer ceramic capacitor may also include a plurality of electrodes. The electrodes may be formed from a variety of suitable conductive materials. For example, the electrodes may be formed from different metals as is known in the art, such as precious metals (e.g., silver, gold, palladium, platinum, etc.), base metals (e.g., copper, tin, nickel, etc.), and so forth, as well as various combinations thereof. However, the electrodes may comprise any suitable conductive material.

Regardless of the particular configuration, the present inventors have discovered that through selective control over the configuration and relative electrical connection of the gas discharge tube and the filter with the conductive line, a compact and robust feedthrough device can be achieved that is particularly suited for protecting a system or subsystem from an electrical transient, for example as caused by an electromagnetic disturbance.

EMPs can be weaponized to harm or incapacitate vehicles, such as planes, helicopters, or tanks. Such EMPs generally include sudden pulses of electromagnetic radiation (e.g., electric and/or magnetic waves) that can induce electrical transients, such as current surges or voltage spikes, in conductive materials. Many systems, such as vehicles, have a conductive outer structure which can act as a columbic shield, like a Faraday cage. The columbic shield can help protect sensitive internal circuits from EMPs.

The presently disclosed feedthrough device may be particularly suited for protecting systems from electromagnetic disturbances, such as EMPs, by providing a gas discharge tube at a location that diverts current before it can damage the protected system. Additionally, the discharge tube may be configured and/or connected to protect sensitive components of the feedthrough device itself, such as the filter. As a result, the feedthrough device may be capable of withstanding a greater magnitude and/or number of electrical transients, such as EMPs.

The feedthrough device may include a gas discharge tube and a filter arranged in a manner that protects the filter from electrical transients. For example, a conductive line may extend through the feedthrough device, and each of the gas discharge tube and filter may be coupled with the conductive line. The gas discharge tube may be coupled with the conductive line at a location that is closer to an input end of the conductive line than the filter. This may allow the gas discharge tube to divert electrical transients before they reach and damage the filter.

Furthermore, the gas discharge tube may also be coupled with the conductive line at a location that is close to where the filter is coupled with the conductive line. As a result, a portion of the conductive line that connects the gas discharge tube with the filter may be relatively short, which may prevent or inhibit an EMP or other electromagnetic disturbance from inducing a significant current in this portion of the conductive line, which could otherwise damage the filter or protected system.

For example, in some embodiments, a distance may be defined between a first location, where the gas discharge is coupled with the conductive line, and a second location, where the filter is coupled with the conductive line. This distance may be short relative to a width of the housing of the feedthrough device. The width may be defined as the largest dimension of the housing in a lateral direction, which is perpendicular to the longitudinal direction in which the conductive line extends. A ratio of the width of the housing to the distance between the first and second locations may be greater than about 5, in some embodiments greater than about 10, in some embodiments greater than about 20, in some embodiments greater than about 30, in some embodiments greater than about 50, and in some embodiments, greater than about 100.

In some embodiments, the distance between the first and second locations on the conductive line may be short relative to a length of the housing of the feedthrough device. The length of the housing may be defined as the longest dimension of the housing in the longitudinal direction. A ratio of the length of the housing to the distance between the first and second locations may be greater than about 5, in some embodiments greater than about 10, in some embodiments greater than about 20, in some embodiments greater than about 30, in some embodiments greater than about 50, and in some embodiments, greater than about 100.

In some embodiments the distance between the first and second locations on the conductive line may be less than 5 cm, in some embodiments less than 2.5 cm, in some embodiments less than about 1 cm, in some embodiments less than about 0.5 cm, and in some embodiments less than about 0.1 cm.

The feedthrough device may also be configured to prevent electrical transients from being induced "after" the gas discharge tube. As used herein, relative terms, such as "before," "after," and "between", generally refer to the relative electrical connectivity of the components along a conductive pathway formed by the conductive line from an input end to an output end of the conductive line. The output end of the conductive line may be connected with the protected system. More specifically, the feedthrough device may be configured to prevent an electromagnetic disturbance, such as an EMP, from inducing a significant current pulse at a location where such a current pulse could reach the protected system. For example, portions of the conductive line after the filter may be effectively shielded by a columbic shield effect formed by the structure (e.g., bulkhead) through which the feedthrough device passes and/or formed by the housing itself.

The gas discharge may have a variety of suitable physical configurations. For example, in some embodiments, the gas discharge tube may include a sealed tube and the gas or gas mixture may be sealed within the tube. The sealed tube may be located inside the housing, for example in a recess or cavity of the housing.

In other embodiments, the gas or gas mixture may be sealed within a cavity of the housing. In such embodiments, the gas discharge tube may not have a separate sealed tube or container to contain the gas. Instead, the cavity of the housing may defined a container for the gas or gas mixture. This may allow the gas discharge tube to be formed immediately adjacent the filter such that the distance along the conductive line between the gas discharge tube and the filter may be minimized. Additionally, this may provide more efficient use of the space within the housing, which may provide for a compact feedthrough that is capable of significant current handling ability.

I. Example Embodiments

FIGS. 1A and 1B illustrate perspective views of embodiments of a feedthrough device configured to mounted in a supporting structure, such as a bulkhead of a vehicle (e.g., aircraft, land vehicle, and/or system or sub-system thereof). FIG. 1A illustrates a feedthrough device 10 that can be threaded into a tapped hole in such supporting structure. The feedthrough device 10 can include a housing 12, which may be electrically connected with the bulkhead such the housing 12 can act as a ground for the feedthrough device 10. For example, the feedthrough device 10 may include a mounting portion 11 that includes threads 13 for engaging complementary threads in the tapped hole in the bulkhead. The feedthrough device 10 may also include a conductive line 14 or pin extending through the housing. The feedthrough device 10 may be configured to filter or otherwise condition electrical signals or power transmission that flows through the conductive line 14. The feedthrough device 10 may also be configured to divert electrical transients, such as current surges or voltage spikes.

FIG. 1B illustrates another feedthrough device 16 that is configured to be soldered, press fit, or otherwise secured in a hole in the bulkhead. The housing 12 may include a mounting portion 11 that is tapered or otherwise shaped for being secured in the hole in the bulkhead. The feedthrough device 16 can generally be configured as the feedthrough device 10 discussed above and may include a housing 12 and conductive line 14.

Figure 2A:
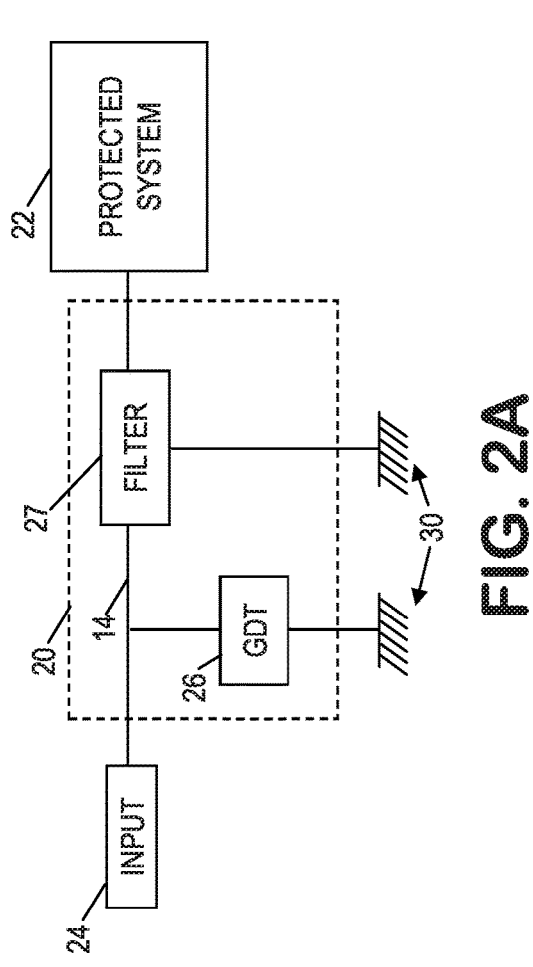
FIG. 2A illustrates a simplified schematic diagram of an embodiment of a feedthrough device connecting a protected system with an input according to aspects of the present disclosure.

FIG. 2A illustrates a simplified schematic diagram of an embodiment of a feedthrough device 20 connecting a protected system 22 with an input 24 according to aspects of the present disclosure. The feedthrough device 20 may include a gas discharge tube 26 and a filter 27. The filter 27 may have a variety of suitable configurations. For example, in some embodiments, the filter 27 may include a capacitor 28 connected with ground 30 as shown in FIG. 2B. In some embodiments, the capacitor 28 may be configured as a multilayer ceramic capacitor 28. Each of the gas discharge tube 26 and capacitor 28 may be coupled with the conductive line 14 and with ground 30. For example, the gas discharge tube 26 and capacitor 28 may be coupled with a housing of the feedthrough device 20, which may act as ground. In other embodiments, a separate ground connection may be provided that is electrically separate from the housing of the feedthrough device. The conductive line 14 may connect the protected system 22 with an input 24. The gas discharge tube 26 may be coupled with the conductive line 14 at a location between the filter 27 and the input 24.

Figure 2C:
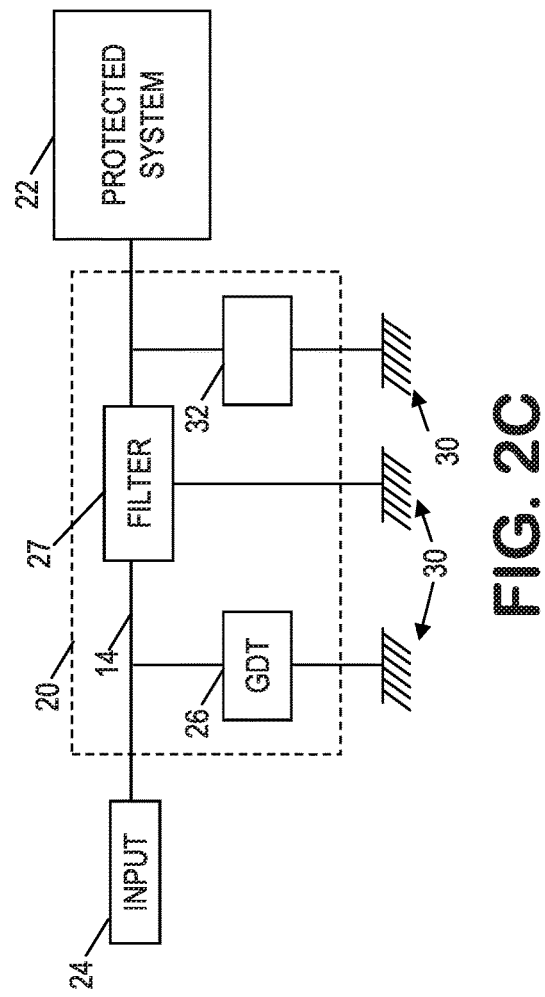
FIG. 2C illustrates a simplified schematic diagram of another embodiment of a feedthrough device connecting a protected system with an input according to aspects of the present disclosure.

FIG. 2C illustrates a simplified schematic diagram of another embodiment a feedthrough device 20 connecting a protected system 22 with an input 24 according to aspects of the present disclosure. In this embodiment, a transient suppression device 32 may be coupled with the conductive line 14 at a location on the conductive line that is between the filter 27 and the protected system 22. As examples, the transient suppression device 32 may include at least one of a diode (e.g., a transient-voltage-suppression diode) or a varistor (e.g., a metal oxide varistor). In other embodiments, the transient suppression device 32 may include a second gas discharge tube. The transient suppression device 32 may be configured to further divert or suppress any remaining current surge or voltage spike that has been transmitted through the filter 111 to protect the protected system 27.

Figure 2D:
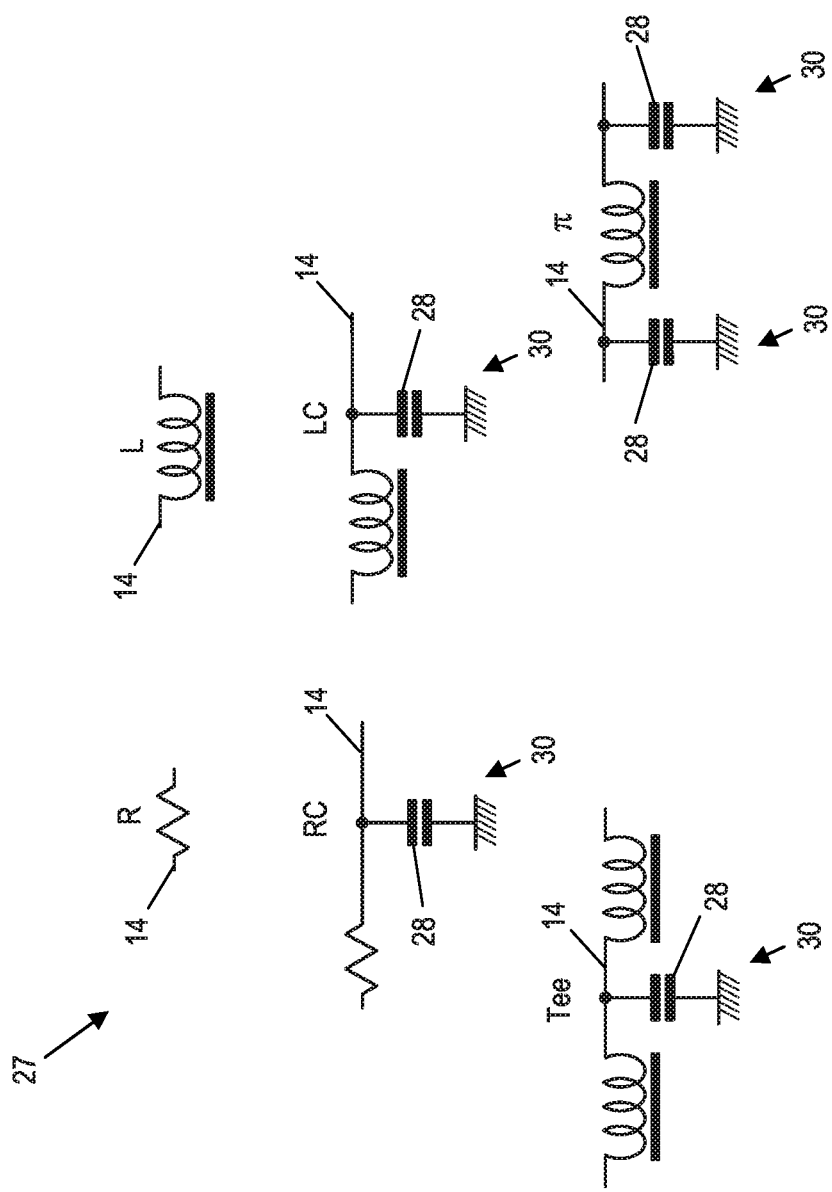
FIG. 2D illustrates additional example configurations for the filter of the feedthrough device of FIG. 2A or FIG. 2C.

FIG. 2D illustrates additional example configurations for the filter 26 of the feedthrough device. In several configurations, a capacitor 28 is coupled between the conductive line 14 and ground 30. Resistors and/or inductors may be employed, for example as illustrated in FIG. 2D, to provide the desired characteristics of the filter 27. It should be understood that these configurations are merely examples, and that the filter 26 may have any suitable configuration depending on the desired characteristics of the filter 27.

Figure 3B:
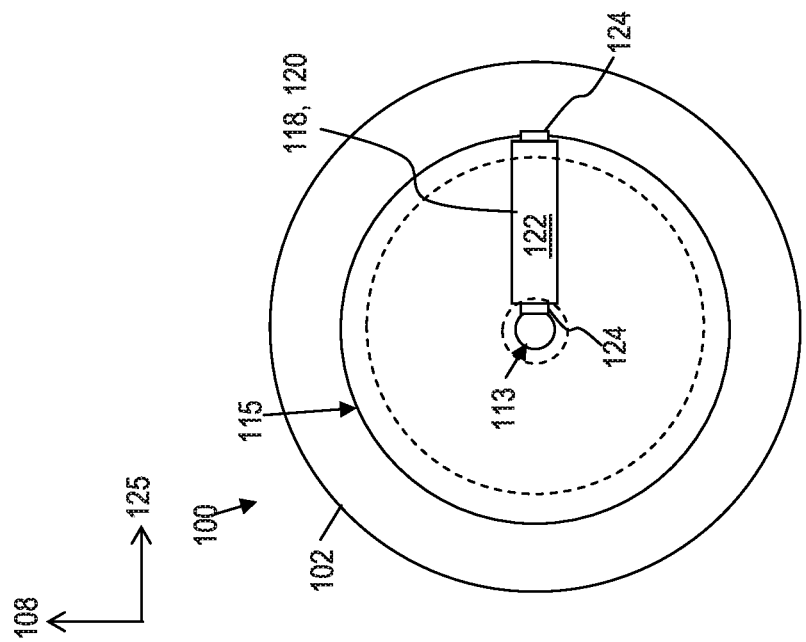
FIG. 3B illustrates a section view of the feedthrough device of FIG. 3A along section A-A.
Figure 3A:
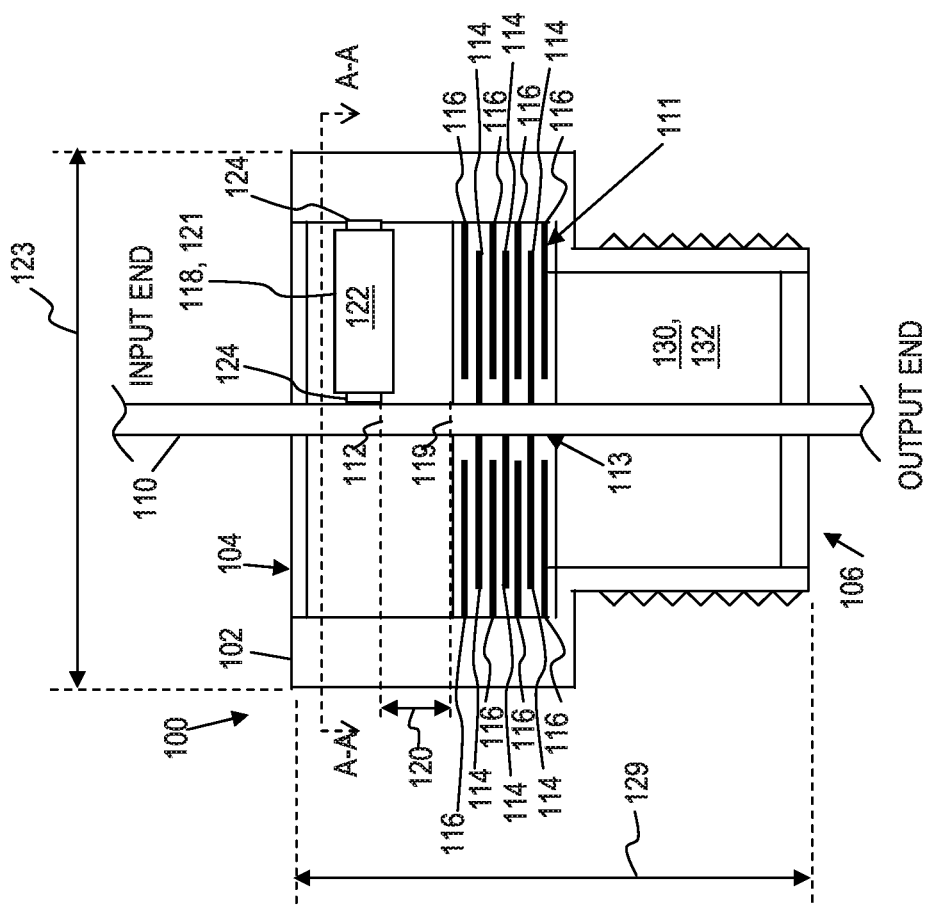
FIG. 3A illustrates a simplified schematic diagram of an embodiment of a feedthrough device according to aspects of the present disclosure.

FIG. 3A illustrates a simplified schematic diagram of a feedthrough device 100 according to aspects of the present disclosure. FIG. 3B illustrates a section view along section A-A of FIG. 3A. The feedthrough device 100 may generally correspond to the feedthrough device 10 described above with reference to FIG. 1A. In some embodiments, the feedthrough device 100 may generally be configured as described and illustrated in FIGS. 2A and 2B. Referring to FIG. 3A, the feedthrough device 100 may include a housing 102 having a first end 104 and a second end 106 which is spaced apart from the first end 104 in a longitudinal direction 108. The feedthrough device 100 may include a conductive line 110 extending through the housing 102 from the first end 104 to the second end 106 of the housing 102.

The feedthrough device 100 may include a filter 111 disposed within the housing 102 and coupled with the conductive line 110 at a first location (represented by dotted line 119). The filter 111 may also be coupled with the housing 102, which may act as ground. In some embodiments, the filter 111 may comprise a multilayer ceramic capacitor that includes a first plurality of layers 114 coupled with the conductive line 110 and a second plurality of layers 116 coupled with the housing 102.

In some embodiments, the multilayer ceramic capacitor may have a discoidal configuration. For example, the multilayer ceramic capacitor may have a generally annular shape. The multilayer ceramic capacitor may define a central through-hole or opening 113, and the conductive line 110 may extend through the opening 113 in the longitudinal direction 108.

The feedthrough device 100 may include a gas discharge tube 118 disposed within the housing 102. The gas discharge tube 118 may be configured to selectively conduct a flow of electricity from the conductive line 110 to the housing 102 when a voltage across the gas discharge tube 118 exceeds a breakdown voltage. In some embodiments, the gas discharge tube 118 may be electrically connected in parallel with the filter 111.

In some embodiments, the gas discharge tube 118 may be coupled with the conductive line 110 at a second location (represented by dotted line 112). The second location 112 may be located between the input end of the conductive line 110 and the first location 119. As such, the gas discharge tube 118 may provide protection from electrical transients (e.g., current surges) at a location that is well suited for protecting the system(s) connected with the output end of the conductive line 110. Additionally, the gas discharge tube 118 may protect the filter 111 from electrical transients by diverting electrical transients to ground (e.g., through the housing 102) before the electrical transients can reach the filter 111.

A distance 120 may be defined between the first location 119 and the second location 112. This distance 120 may be relatively short. In other words, the portion of the conductive line 110 connecting the gas discharge tube 118 with the filter 111 may be relatively short. Electromagnetic disturbances, such as an EMPs, may be prevented from inducing a significant electrical current in this portion of the conductive line 110 which could otherwise damage the filter 111 or pass through the feedthrough device 100 and damage the protected system.

For example, in some embodiments, the distance 120 may be short relative to a width 123 of the housing 102 of the feedthrough device 100. The width 100 may be defined as the largest dimension of the housing in a lateral direction 125, which is perpendicular to the longitudinal direction 108. In some embodiments, the housing 102 may have a circular cross section such that the width 123 corresponds a diameter of the housing 102. A ratio of the width 123 of the housing 102 to the distance 120 between the first location 119 and second location 112 may be greater than about 5.

In some embodiments, the distance 120 between the first location 119 and second location 112 on the conductive line 110 may be short relative to a length 129 of the housing 102. The length 129 may be defined as the longest dimension of the housing 102 in the longitudinal direction 108. A ratio of the distance 120 and the length 129 of the housing 102 may be greater than about 5. Additionally, in some embodiments, the distance 120 may be less than 5 cm.

It should be understood that in some embodiments the portion of the conductive line 110 between the first location 119 and the second location 112 may be curved or contain one or more curved or bent sections. In such embodiments, the distance 120 between the first location 119 and second location 112 may be defined as the distance along the conductive line 110 that an electrical current would travel from the first location 119 to the second location 112.

In some embodiments, the gas discharge tube 118 may extend radially outward from the conductive line 110 to the housing 102. The gas discharge tube 118 may include a sealed tube 121 and a gas or gas mixture 122 contained within the tube 210. The gas discharge tube 118 may also include a pair of terminals 124 or electrodes. The gas mixture 122 may be configured to ionize when the voltage across the gas discharge tube 118 (e.g., across the terminals 124 of the gas discharge tube 118) becomes sufficiently great. The ionized gas mixture 122 may then permit current to flow between the pair of terminals 124 from the conductive line 110 to the housing 102.

FIG. 4A illustrates a simplified schematic diagram of another embodiment of a feedthrough device 100 according to aspects of the present disclosure. FIG. 4B illustrates a section view along section A-A of FIG. 4A. In some embodiments, the gas discharge tube 118 may be defined as a gas contained within a cavity formed by the housing 102. For example, instead of a sealed tube that contains a gas as described above with reference to FIGS. 3A and 3B, the gas discharge tube may include a cavity 126 formed by the housing 102 and/or a surface of the filter 111. The gas mixture 122 may be contained within this cavity 126. For example, the housing 102 may include one or more seals 128 configured to seal the gas mixture 122 inside the cavity 126. A portion of the conductive line 110 may extend through the cavity 126. In some embodiments, the portion of the conductive line 110 may directly electrically contact the gas mixture 122 in the cavity 126. In other embodiments, a conductive layer (e.g., a coating) of conductive material may be formed around an exterior of the conductive line 110. For example, the conductive layer may be formed from a variety of suitable materials including precious metals (e.g., silver, gold, palladium, platinum, etc.), base metals (e.g., copper, tin, nickel, etc.), and so forth, as well as various combinations thereof.

In such embodiments, the distance (represented by 120 in FIG. 3A) may be negligibly small. In other words, the cavity 126 may be located directly adjacent the filter 111. For example, a wall of the cavity 126 may be defined by an outer layer 131 (e.g., a dielectric layer or casing) of the filter 111. This may prevent or hinder an electromagnetic disturbance, such as an EMP, from inducing a current in the conductive line 110 at a location that can harm the filter 111 or pass through the feedthrough device 100. As indicated above, in some embodiments, the filter 111 may be sufficiently protected by a columbic shield effect produced by the housing 102 and/or by the bulkhead or other structure in which the feedthrough device 100 is secured.

Figure 5B:
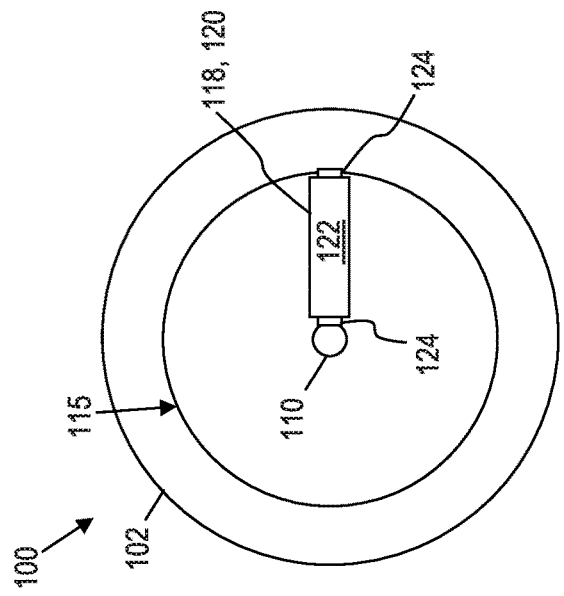
FIG. 5B illustrates a section view of the feedthrough device of FIG. 5A along section A-A.
Figure 5C:
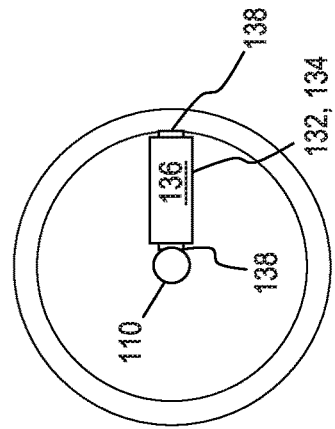
FIG. 5C illustrates a section view of the feedthrough device of FIG. 5A along section B-B.
Figure 5A:
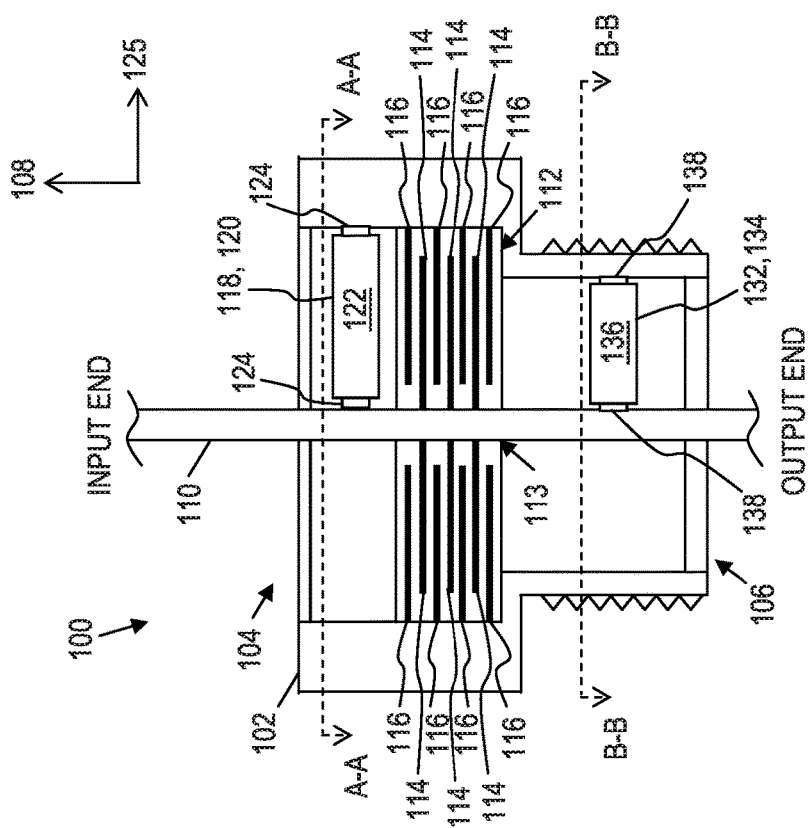
FIG. 5A illustrates a simplified schematic diagram of another embodiment of a feedthrough device according to aspects of the present disclosure.

FIG. 5A is a simplified schematic diagram of another embodiment of the feedthrough device 100 according to aspects of the present disclosure. FIG. 5B is a section view along section A-A of FIG. 5A. FIG. 5C is a section view along section B-B of FIG. 5A. In some embodiments, a passive transient suppression device 132 may be coupled with the conductive line 110 at a location on the conductive line that is between the filter 111 and the output end of the conductive line 110. As examples, the passive transient suppression device 132 may include at least one of a diode (e.g., a transient-voltage-suppression diode) or a varistor (e.g., a metal oxide varistor). In other embodiments, the passive transient suppression device 132 may include a second gas discharge tube including a sealed tube 134 and a gas 136 therein, for example in a similar manner as the gas discharge tube 118 described above. The second gas discharge tube may include a pair of terminals 138 and may be coupled with each of the conductive line 110 and the housing 102. For example, such a configuration may be schematically represented by FIG. 2C.

Figure 6A:
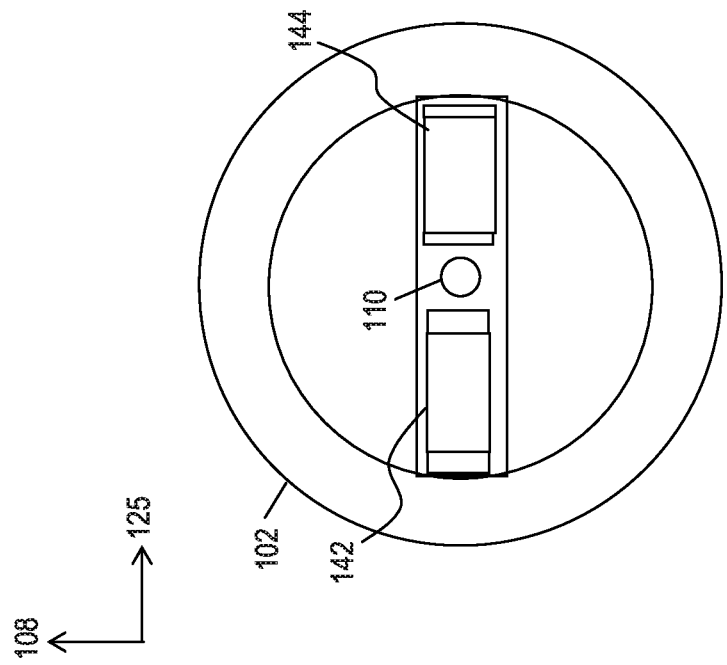
FIG. 6A illustrates a simplified schematic diagram of another embodiment of the feedthrough device according to aspects of the present disclosure.
Figure 6B:
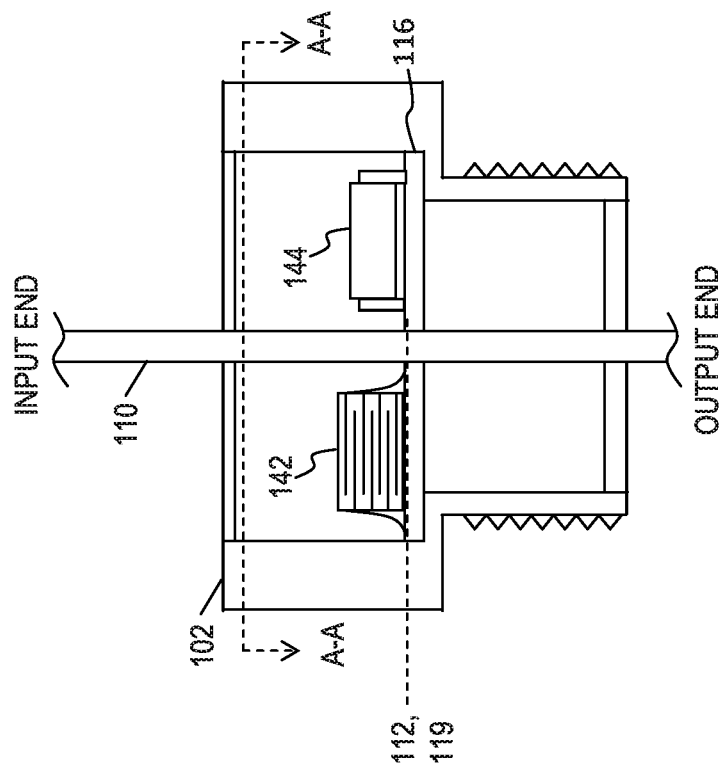
FIG. 6B illustrates a section view of the feedthrough device of FIG. 6A along section A-A.

FIG. 6A is a simplified schematic diagram of another embodiment of the feedthrough device 100 according to aspects of the present disclosure. FIG. 6B is a section view along section A-A of FIG. 6A. In some embodiments, the feedthrough device 100 may include a printed circuit board 140 or other suitable substrate for surface mounting one or more components. The printed circuit board 140 may be disposed within the housing 102 such that such that the printed circuit 140 may electrically couple one or more surface mounted components to the housing 102 and/or the conductive line 110. For example, the feedthrough device 100 may include a surface mount multilayer ceramic capacitor 142. The surface mount multilayer capacitor 142 may include a monolithic substrate and a plurality of interdigitated layers. The surface mount multilayer ceramic capacitor 142 may be mounted to the printed circuit board 140, and the printed circuit board 140 may couple the surface mount multilayer ceramic capacitor 142 with conductive line 110 and the housing 102. The feedthrough device 100 may also include a surface mount gas discharge tube 144, which may be mounted to the printed circuit board 140. The printed circuit board 140 may couple the surface mount gas discharge tube 144 with conductive line 110 and the housing 102. For example, such a configuration may be schematically represented by FIG. 2A, in which the filter 27 is configured as illustrated in FIG. 2B.

In such embodiments, the printed circuit board may facilitate electrical connection of the surface mount multilayer ceramic capacitor 142 and the surface mount gas discharge tube 144 at effectively the same location along the conductive line 110. In other words, the distance (represented by 120 in FIG. 3A) may be negligibly small or effectively zero.

It should be understood that various combination and/or variations of the disclosed subject matter are possible within the scope of this disclosure. For example, in some embodiments the feedthrough device 100 may include a printed circuit board having at least one surface mount component mounted thereon in combination with at least one of a discoidal multilayer capacitor or a gas discharge tube that is formed within a cavity of the housing 102 of the feedthrough device 100. In other embodiments, the feedthrough device 100 may include a gas discharge tube including a sealed tube, for example as described above with reference to FIGS. 3A and 3B, in combination with a second gas discharge tube that is formed within a cavity of the hosing. For example, referring back to FIG. 3A, in some embodiments a second cavity 130 may be formed within the housing 102 between the filter 111 and the output end of the conductive line 110. The cavity 130 may be filled with a gas or gas mixture to form a second gas discharge tube 146. For example, such a configuration may be schematically represented by FIG. 2C in which the second gas discharge tube 146 is represented by the transient suppression device 32. One of ordinary skill in the art should understand that yet other combinations and/or variations are possible within the scope of this disclosure.

II. Applications

The feedthrough assembly may be used to protect any system or sub-system from electrical transients. The feedthrough assembly may also be used to couple the system or sub-system with a communication line or power line.

The feedthrough assembly may find particular application in the protection of vehicles from a large electrical transient, such as an electro-magnetic pulse (EMP). Such pulses can damage or temporarily incapacitate electrical systems. The disclosed feedthrough assembly can be employed at a location that diverts such pulses away from sensitive electronics. For example, many vehicles have a conductive outer structure, which can act as a Faraday cage, electrically protecting sensitive electrical components contained therein. The disclosed feedthrough assembly can be connected with the vehicle at a location such that an electrical transient is diverted to the outer structure, thereby preserving the columbic-shield properties of the outer structure.

Example vehicles include air vehicles (e.g., airplanes, helicopters, etc.), land vehicles (e.g., trucks, tanks, etc.), and water vehicles (e.g., ships, sub-marines, amphibious vehicles, etc.). In some implementations, the feedthrough assembly may be used to preserve Faraday properties of a structure contained within or partially within an outer structure of the vehicle. For example, the feedthrough assembly may be mounted to a bulkhead or other structural component such that an electrical signal or power supply may be connected or supplied through the feedthrough device (e.g., from one compartment to another compartment and/or into a system or sub-system of the vehicle). For instance, the feedthrough assembly may be used to provide electrical connection between two systems or sub-systems of a vehicle (e.g., a radio system, navigation system, control system, and/or any sub-system thereof).

The feedthrough device may also find application with medical devices, including implantable devices. For example, cardiac pacemakers, defibrillators, and the like may be implanted into a patient and configured to deliver a therapeutic shock treatment to the heart of the patient. Such devices generally employ one or more power sources, such as a battery or capacitor. The power source is contained within a housing of the device, and one or more electrodes are disposed near the heart of the patient for delivering the therapeutic shock treatment to the heart. Such devices may include a feedthrough device according to aspects of the present disclosure to couple the electrode(s) with the power source. The presently disclosed feedthrough device may be useful for protecting the internal circuitry of the implantable devices from electrical transients (e.g., interference, current surges, etc.,) that may be induced in the electrodes or associated leads of the device.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A bulkhead feedthrough device for protecting a system from an electrical transient, the feedthrough device comprising:
    a housing having a first end and a second end spaced apart from the first end in a longitudinal direction;
    a conductive line extending in the longitudinal direction through the housing from the first end to the second end of the housing, the conductive line defining an input end proximate the first end of the housing and an output end proximate the second end of the housing for connecting the feedthrough device with the system;
    an alternating current filter disposed within the housing and electrically connected with the conductive line at a first location; and
    a gas discharge tube disposed within the housing and electrically connected with the conductive line at a second location on the conductive line that is proximate the filter, the second location being between the input end of the conductive line and the first location with respect to the longitudinal direction.

2. The bulkhead feedthrough device of claim 1, wherein the housing has a width in a lateral direction that is perpendicular to the longitudinal direction, and wherein a ratio of the width of the housing to a distance between the first location and the second location is greater than about 5.

3. The bulkhead feedthrough device of claim 1, wherein the housing has a length in the longitudinal direction, and wherein a ratio of the length of the housing to a distance between the first location and the second location is greater than about 5.

4. The bulkhead feedthrough device of claim 1, wherein a distance between the first location and the second location is less than 5 cm.

5. The bulkhead feedthrough device of claim 1, wherein the alternating current filter comprises a multilayer ceramic capacitor that comprises a first plurality of layers electrically connected with the conductive line and a second plurality of layers electrically connected with the housing.

6. The bulkhead feedthrough device of claim 1, wherein the alternating current filter comprises a discoidal multilayer ceramic capacitor.

7. The bulkhead feedthrough device of claim 6, wherein the conductive line extends through the discoidal multilayer ceramic capacitor in the longitudinal direction.

8. The bulkhead feedthrough device of claim 1, wherein the alternating current filter comprises at least one of a varistor, diode, or inductor.

9. The bulkhead feedthrough device of claim 1, wherein the gas discharge tube comprises a sealed tube and a gas contained within the tube.

10. The bulkhead feedthrough device of claim 9, wherein the gas discharge tube extends radially outward from the conductive line to the housing.

11. The bulkhead feedthrough device of claim 1, wherein:
the housing defines a cavity;
a portion of the conductive line extends through the cavity; and
the gas discharge tube comprises a gas contained within the cavity that is electrically connected with each of the housing and the portion of the conductive line that extends through the cavity.

12. The bulkhead feedthrough device of claim 1, wherein the gas discharge tube is configured to selectively conduct a flow of electricity from the conductive line to at least one of the housing or a separate ground when a voltage across the gas discharge tube exceeds a breakdown voltage.

13. The bulkhead feedthrough device of claim 1, further comprising a printed circuit board, and wherein at least one of the multilayer ceramic capacitor or the gas discharge tube is mounted on the printed circuit board.

14. The bulkhead feedthrough device of claim 13, wherein the multilayer ceramic capacitor and the gas discharge tube are each mounted to the printed circuit board and electrically connected with the conductive line at substantially the same location along the conductive line.

15. The bulkhead feedthrough device of claim 1, further comprising a passive transient suppression device electrically connected with the conductive line between the alternating current filter and the output end of the conductive line.

16. The bulkhead feedthrough device of claim 15, wherein the passive transient suppression device comprises at least one of a varistor, diode, or inductor coupled with the conductive line.

* * * * *